US00PP08825P

United States Patent [19]

Patterson

[11] Patent Number: Plant 8,825

[45] Date of Patent: Jul. 12, 1994

[54] FEIJOA VARIETY NAMED OPAL STAR

[75] Inventors: Kevin Patterson; Lawrence E. Hedley, both of Auckland, New Zealand

[73] Assignee: Horticultural and Food Research Institute of New Zealand Limited, Palmerston North, New Zealand

[21] Appl. No.: 984,056

[22] Filed: Nov. 30, 1992

[51] Int. Cl.[5] ..... A01H 5/00

[52] U.S. Cl. ..... Plt./33.1

[58] Field of Search ..... Plt. 33.1

[56] References Cited

PUBLICATIONS

Application for Plant Variety Rights.

Technical Questionnaire.

Objective Description of Variety.

*Primary Examiner*—James R. Feyrer

*Assistant Examiner*—Bruce Campbell

*Attorney, Agent, or Firm*—Quarles & Brady

[57] ABSTRACT

The new and distinct variety is a Feijoa designated Opal Star. The Opal Star variety is characterized by a lower tree height and spread than the Appolo variety, more lateral branching than the Triumph variety and a fruit having a smoother skin and a higher productivity than Triumph and a smaller size than Appolo. The variety is further distinguished by its late season maturity, heavy cropping and moderately compact habit.

4 Drawing Sheets

SUMMARY OF THE INVENTION

The present invention relates to a new and distinct Feijoa variety. The variety is a seedling of unknown parentage. The variety is distinguished by its late season maturity, heavy cropping and moderately compact habit.

The variety was the result of open pollination of unknown seed and pollen parents. After the variety was selected in 1981 in Auckland, New Zealand it was reproduced by grafting onto Feijoa seedling rootstock at Hort Research Orchards in Kumeu, New Zealand. Asexual propagation shows that the unique combination of characteristics come true to form and are established and transmitted through succeeding propagations. The new variety has been named Opal Star.

BRIEF DESCRIPTION OF THE PHOTOGRAPH

The invention may be more fully understood by having reference to the accompanying color photograph which shows as nearly true as is reasonably possible to make the same in a color illustration of this character typical specimens of the variety.

FIG. 1: Shows the whole fruit, cross section of fruit, leaves and flowers.

FIG. 2: Shows the Opal Star Feijoa tree claimed.

FIG. 3: Shows the claimed variety, including fruits and leaves on the tree.

FIG. 4: Shows the bark of the claimed variety.

DETAILED DESCRIPTION

The following is a detailed description of the new variety with color terminology in accordance with a Minolta Color meter on 20 fruit and 20 leaves sampled from 10 trees using the L,a,b system.

All colour designations made herein are made with reference to the Pantone System.

The distinctive characteristics of the new Feijoa cultivar described in detail below were observed in the 1987 season. The specimens were grown at the HortResearch Orchard in Kumeu, New Zealand. The trees were four years old.

In comparison to Triumph, Opal Star has a smoother skin, more lateral branching, is mature 1 week before and generally yields approximately 10% more fruit of marketable size (>65 g). In comparison to Apollo, Opal Star has a fruit size that is generally smaller, and a lower tree height and spread than Apollo with less detailed pruning required to achieve high yields.

Figure 2:
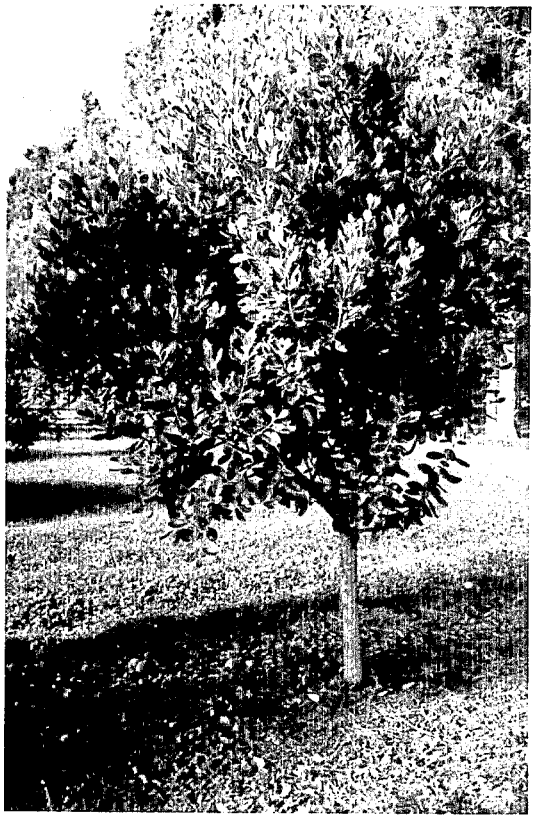
Figure 4:
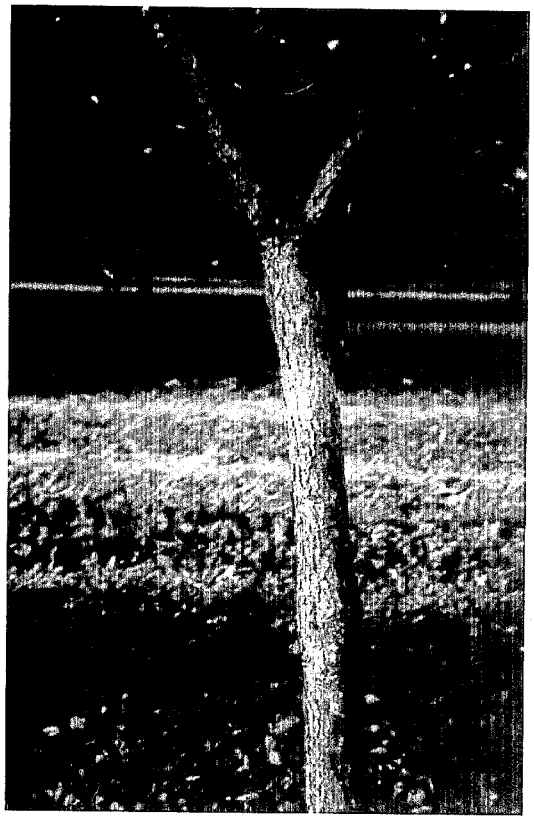

Tree: Upright monopodial spreading habit with a high propensity for lateral branching on the current season's growth; medium vigour; short internode length (<25 mm); branching of current seasons growth is high; a more compact tree form than vigorous upright cultivars such as Appolo; smooth, young, light reddish-brown bark, shown in FIG. 4, that becomes grey to light brown and flaky with age. The colour of the bark is a non-uniform composite which cannot, therefore, be described using a recognized colour system; Opal Star is an evergreen, even in locations having a temperate climate; tree height of ten 10-year old trees growing at Kumeu Research Orchard ranged from 1.9 to 2.2 meters; maximum canopy width of the 10-year old trees ranged from 1.8 to 2 meters at approximately 1.3 meters above the ground; see FIG. 2.

Figure 1:
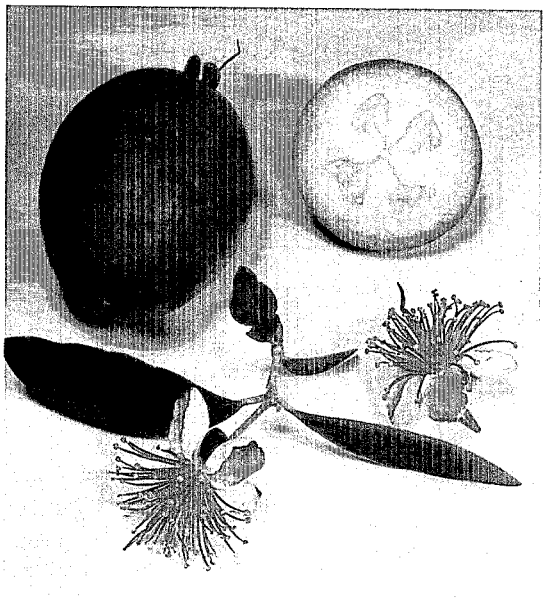

Flowers: Mainly unistylar; 4 or 5 petals; 4 or 5 sepals; 40 to 60 stamens; 4 to 6 flowers per inflorescence; see FIG. 1.

Pollination: Self infertile; suitable pollinators include Apollo, Triumph, Gemini and Unique; heavy bloom; very high fruitset; fruitlet thinning required to maximise fruit size.

Mature current season leaves: Lamina length, 66 mm; width 33 mm; length/width ratio, 2; mainly elliptic leaf shape; mainly straight margin; tendency for leaves to alternate on branches; have three leaves per node; have fasciated apices; no variegation present.

Figure 3:
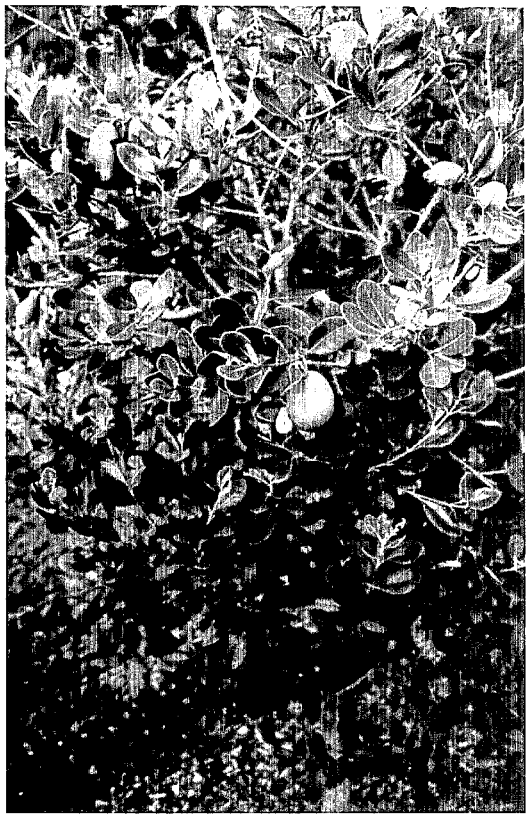

Leaf color: Leaf colours of twenty leaves sampled from ten Opal Star trees on May 24, 1993 was Pantone 574C on the adaxial surface and was closest to Pantone 5585C on the hirsute underside (abaxial surface); see FIG. 3.

FRUIT

Size: Large (76–100 g); length, 63 mm; width, 49 mm; length to width ratio, 1.28.

Shape: Obovoid; symmetric; depressed basal outline; mainly oblong outline of peduncle scar; open calyx orientation.

Skin: Dark green color, comparable to Gemini; skin colours of twenty fruit selected from ten Opal Star trees on May 24, 1993 were defined using a Pantone 747XR Colour Formula Guide and ranged from Pantone 371C to 377U; smooth; no skin pitting; no prominent grooves on fruit surface.

Skin color: L 47.8, a -13.6, b 29.4.

Locules: Four, locule development as a percentage of cross sectional areas, 30–45%; flesh thickness between locules, >5 mm; central axis of fruit; gelatinous; white/opaque pulp appearance at harvest; cream seed color at harvest.

Flesh: Smooth texture with a minimum of grittiness; strong aromatic flavour with a good sugar acid balance; fruit generally considered too acidic to eat directly from the tree; firmness at harvest is typically 3 to 4 kg which reduces to about 1 to 2 kg after 10 days.

Flesh color: Pantone 461C (1 mm below the skin surface).

Maturity: Late season; 1 week before Triumph and 4 weeks after Unique, maturation over a 5 to 6 week harvest from late April to late May, Auckland, New Zealand.

Yield: High yielding cultivar relative to Triumph; cropping normally commencing in third year; yields of 30 kg tree typical for trees in their fifth year after planting.

Storage: Four weeks at 3 degrees C. with 5 days shelf life if harvested by 'touch pick' method.

Shelf life: Fruit harvested by 'touch pick' method have a shelf life of 10 days at 20 degrees C. and are ready to eat approximately 3 days after harvest.

I claim:

1. A new and distinct variety of Feijoa substantially as illustrated and described which is characterized by its late season harvest, heavy cropping and moderately compact habit.

* * * * *